US011995744B2

(12) United States Patent
Feng et al.

(10) Patent No.: US 11,995,744 B2
(45) Date of Patent: May 28, 2024

(54) SYSTEMS AND METHODS FOR POSITRON EMISSION TOMOGRAPHY IMAGING

(71) Applicant: SHANGHAI UNITED IMAGING HEALTHCARE CO., LTD., Shanghai (CN)

(72) Inventors: Tao Feng, Houston, TX (US); Yang Lyu, Shanghai (CN); Hao Liu, Shanghai (CN); Gang Yang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 733 days.

(21) Appl. No.: 17/138,867

(22) Filed: Dec. 30, 2020

(65) Prior Publication Data
US 2022/0207792 A1    Jun. 30, 2022

Related U.S. Application Data

(63) Continuation of application No. 16/956,028, filed as application No. PCT/EP2018/086442 on Dec. 20, 2018, now Pat. No. 11,461,582.
(Continued)

(51) Int. Cl.
*G06K 9/62* (2022.01)
*A61B 6/00* (2006.01)
(Continued)

(52) U.S. Cl.
CPC .......... *G06T 11/005* (2013.01); *A61B 6/037* (2013.01); *A61B 6/5264* (2013.01);
(Continued)

(58) Field of Classification Search
CPC .............. G06T 11/005; G06T 2210/41; G06T 2211/412; A61B 6/037; A61B 6/5264; A61B 6/5282; G01T 1/2985
(Continued)

(56) References Cited

U.S. PATENT DOCUMENTS 10,398,382 B2   9/2019  Sanders et al.
11,179,128 B2 * 11/2021 Heukensfeldt Jansen ..................
                                                        A61B 6/037
(Continued)

FOREIGN PATENT DOCUMENTS

CN    105496436 A   *  4/2016  ............. A61B 6/037
CN    109741284    *  6/2021  ................ G06T 7/11
WO    WO2006109203 * 10/2006  ............ G06T 11/005

OTHER PUBLICATIONS

F Lamare et al., List-mode-based Reconstruction for Respiratory Motion Correction in PET Using Non-rigid Body Transformations, Physics in Medicine and Biology, 52: 5187-5204, 2007.

Primary Examiner — Jerome Grant, II
(74) Attorney, Agent, or Firm — METIS IP LLC

(57) ABSTRACT

An imaging method may include obtaining original imaging data of an object in a raw-data domain including original time of flight (TOF) information. The method may also include gating the original imaging data into a plurality of data sets in the raw-data domain. The method may also include determining a plurality of motion vector fields based on the plurality of data sets. The method may also include generating corrected imaging data in the raw-data domain by performing motion correction on at least one of the plurality of data sets based on the original TOF information and at least one corresponding MVF of the plurality of MVFs. The method may also include generating one or more target
(Continued)

images of the object by performing, based on the corrected imaging data, image reconstruction.

20 Claims, 11 Drawing Sheets

Related U.S. Application Data

(60) Provisional application No. 62/608,352, filed on Dec. 20, 2017.

(51) Int. Cl.
*A61B 6/03* (2006.01)
*G01T 1/29* (2006.01)
*G06T 11/00* (2006.01)

(52) U.S. Cl.
CPC .......... *A61B 6/5282* (2013.01); *G01T 1/2985* (2013.01); *G06T 2210/41* (2013.01)

(58) Field of Classification Search
USPC ........................................................ 382/157
See application file for complete search history.

(56) References Cited

U.S. PATENT DOCUMENTS

| | | | |
|---|---|---|---|
| 2009/0253980 A1* | 10/2009 | Wollenweber | A61B 6/037 600/410 |
| 2013/0182928 A1* | 7/2013 | Park | G06T 5/50 382/131 |
| 2013/0197347 A1* | 8/2013 | Moghari | G01R 33/56509 600/410 |
| 2021/0104037 A1* | 4/2021 | Schleyer | G06T 7/0012 |
| 2021/0124003 A1* | 4/2021 | Lazarus | G01R 33/5608 |
| 2021/0264590 A1* | 8/2021 | Milioni De Carvalho | G06T 7/0012 |

* cited by examiner

1100

| For each of a plurality of original LOR sections of an original LOR of a data set, determining a transformed LOR section by performing, based on the motion vector field corresponding to the data set, rigid transformation on the original LOR section | ← 1110 |

↓

| Determining transformed TOF information corresponding to the transformed LOR section by performing, based on the motion vector field corresponding to the data set, the rigid transformation on original TOF information of the original LOR section | ← 1120 |

↓

| Determining, based on the motion vector field corresponding to the data set and the rigid transformation on original detector locations of two first detector units, transformed detector locations of two second detector locations | ← 1130 |

↓

| Generating corrected imaging data based on at least one of the transformed LOR sections, the transformed TOF information corresponding to the transformed LOR sections, or the transformed detector locations corresponding to the transformed LOR sections | ← 1140 |

FIG. 11

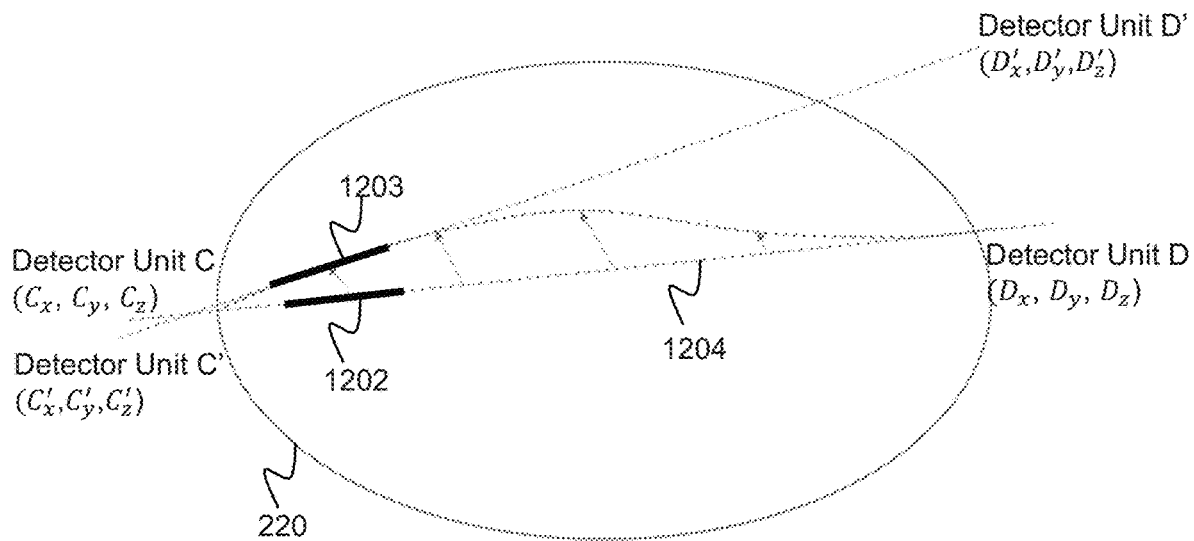
FIG. 12
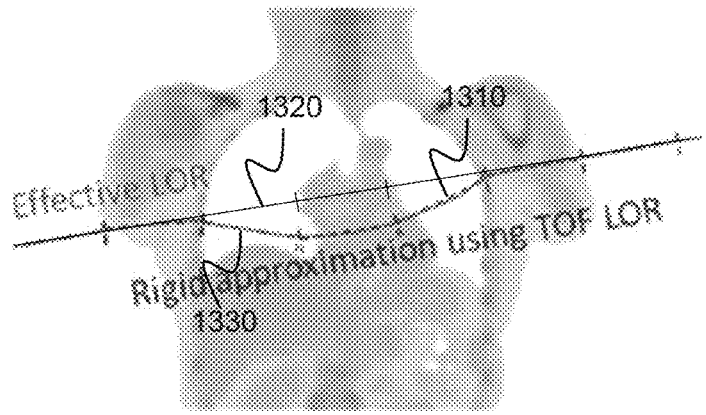
FIG. 13
1400
Generating a sensitivity map based on the transformed detector locations corresponding to the each of the transformed LOR sections — 1410
Generating one or more images of an object based on the corrected imaging data and the sensitivity map — 1420
FIG. 14

SYSTEMS AND METHODS FOR POSITRON EMISSION TOMOGRAPHY IMAGING

TECHNICAL FIELD

The present disclosure generally relates to positron emission tomography (PET), and more specifically relates to systems and methods for non-rigid motion correction in PET.

BACKGROUND

Positron Emission Tomography (PET) is a technology developed in nuclear medicine. It is non-invasive and able to provide high-quality images. A radioactive substance is administered to a patient. An imaging detector detects the γ-radiation emitted from the patient. The detected emissions are tomographically reconstructed to generate an image of locations of the emissions in a patient. Due to motion (e.g., non-rigid motion such as respiration motion) during detection, the reconstructed image may include motion artifacts or be blurred.

SUMMARY

According to a first aspect of the present disclosure, an imaging system may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain original imaging data of an object in a raw-data domain. The original imaging data may be acquired by an imaging device. The original imaging data may include original time of flight (TOF) information and may be subject to non-rigid motion of the object. The one or more processors may gate the original imaging data into a plurality of data sets in the raw-data domain each of which corresponds to a motion phase of the non-rigid motion. The one or more processors may determine a plurality of motion vector fields (MVFs) based on the plurality of data sets. The plurality of motion vector fields may indicate the non-rigid motion. Each of the plurality of motion vector fields may correspond to one of the plurality of data sets. The one or more processors may generate corrected imaging data in the raw-data domain by performing motion correction on at least one of the plurality of data sets based on the original TOF information and at least one corresponding MVF of the plurality of MVFs. The one or more processors may generate one or more target images of the object by performing, based on the corrected imaging data, image reconstruction.

In some embodiments, to generate corrected imaging data by performing motion correction on at least one of the plurality of data sets based on the original TOF information and at least one corresponding MVF of the plurality of MVFs, for an original line of response (LOR) of one of at least one of the plurality of data sets, the one or more processors may divide, based on the original TOF information, the original LOR into a plurality of original LOR sections. The one or more processors may generate the corrected imaging data by performing, based on the corresponding MVF, rigid transformation on the plurality of original LOR sections.

In some embodiments, a length of each of the plurality of original LOR sections may depend on temporal resolution of the original TOF information.

In some embodiments, to generate the corrected imaging data by performing, based on the corresponding MVF, rigid transformation on the plurality of original LOR sections, for each of the plurality of original LOR sections of the original LOR of the data set, the one or more processors may determine a transformed LOR section by performing, based on the corresponding MVF, the rigid transformation on the original LOR section. The one or more processors may generate the corrected imaging data based on the transformed LOR sections.

In some embodiments, to generate the corrected imaging data by performing, based on the corresponding MVF, rigid transformation on the plurality of original LOR sections, for each of the transformed LOR sections, the one or more processors may determine transformed TOF information corresponding to the transformed LOR section by performing, based on the corresponding MVF, the rigid transformation on the original TOF information of the corresponding original LOR section. The one or more processors may generate the corrected imaging data based further on the transformed TOF information corresponding to the transformed LOR sections.

In some embodiments, to generate the corrected imaging data by performing, based on the corresponding MVF, rigid transformation on the plurality of original LOR sections, for each of the transformed LOR sections, the one or more processors may determine, based on the corresponding MVF and the rigid transformation on original detector locations of two first detector units, transformed detector locations of two second detector locations. The two first detector units may be two of a plurality of detector units of the imaging device and correspond to the original LOR. The two second detector units may be two of the plurality of detector units of the imaging device and correspond to the transformed LOR section. The one or more processors may generate the corrected imaging data based further on the transformed detector locations corresponding to the each of the transformed LOR sections.

In some embodiments, the one or more processors may generate a sensitivity map based on the transformed detector locations corresponding to the each of the transformed LOR sections. The one or more processors may generate the one or more target images of the object based further on the sensitivity map.

In some embodiments, the original LOR that is a straight line may be transformed, due to the non-rigid motion, into an effective LOR that is a non-straight line.

In some embodiments, the effective LOR may be approximated by the transformed LOR sections corresponding to the plurality of original LOR sections of the original LOR.

In some embodiments, each of the transformed LOR sections may be a straight line.

In some embodiments, the one of the at least one of the plurality of data set may include a plurality of coincidence events corresponding to the original LOR. Each of the plurality of original LOR sections may correspond to one of the plurality of coincidence events.

In some embodiments, the original imaging data in the raw-data domain may include listmode data or sinogram data.

In some embodiments, the non-rigid motion may include respiration motion or cardiac motion of the object.

In some embodiments, to generate the one or more images of the object based on the corrected imaging data, the one or more processors may obtain an attenuation map of the object. The one or more processors may generate the one or more target images of the object based on the corrected imaging data and the attenuation map.

In some embodiments, to obtain an attenuation map of the object, the one or more processors may determine the attenuation map based on the plurality of motion vector fields.

According to another aspect of the present disclosure, an imaging method may include one or more of the following operations. One or more processors may obtain original imaging data of an object in a raw-data domain. The original imaging data may be acquired by an imaging device. The original imaging data may include original time of flight (TOF) information and may be subject to non-rigid motion of the object. The one or more processors may gate the original imaging data into a plurality of data sets in the raw-data domain each of which corresponds to a motion phase of the non-rigid motion. The one or more processors may determine a plurality of motion vector fields (MVFs) based on the plurality of data sets. The plurality of motion vector fields may indicate the non-rigid motion. Each of the plurality of motion vector fields may correspond to one of the plurality of data sets. The one or more processors may generate corrected imaging data in the raw-data domain by performing motion correction on at least one of the plurality of data sets based on the original TOF information and at least one corresponding MVF of the plurality of MVFs. The one or more processors may generate one or more target images of the object by performing, based on the corrected imaging data, image reconstruction.

According to yet another aspect of the present disclosure, an imaging system may include an obtaining module configured to obtain original imaging data of an object in a raw-data domain. The original imaging data may be acquired by an imaging device. The original imaging data may include original time of flight (TOF) information and may be subject to non-rigid motion of the object. The system may also include a gating module configured to gate the original imaging data into a plurality of data sets in the raw-data domain each of which corresponds to a motion phase of the non-rigid motion. The system may also include a motion field determination module configured to determine a plurality of motion vector fields (MVFs) based on the plurality of data sets. The plurality of motion vector fields may indicate the non-rigid motion. Each of the plurality of motion vector fields may correspond to one of the plurality of data sets. The system may also include a motion correction module configured to generate corrected imaging data in the raw-data domain by performing motion correction on at least one of the plurality of data sets based on the original TOF information and at least one corresponding MVF of the plurality of MVFs. The system may also include a reconstruction module configured to generate one or more target images of the object by performing, based on the corrected imaging data, image reconstruction.

According to yet another aspect of the present disclosure, a non-transitory computer readable medium may comprise at least one set of instructions. The at least one set of instructions may be executed by one or more processors of a computing device. The one or more processors may obtain original imaging data of an object in a raw-data domain. The original imaging data may be acquired by an imaging device. The original imaging data may include original time of flight (TOF) information and may be subject to non-rigid motion of the object. The one or more processors may gate the original imaging data into a plurality of data sets in the raw-data domain each of which corresponds to a motion phase of the non-rigid motion. The one or more processors may determine a plurality of motion vector fields (MVFs) based on the plurality of data sets. The plurality of motion vector fields may indicate the non-rigid motion. Each of the plurality of motion vector fields may correspond to one of the plurality of data sets. The one or more processors may generate corrected imaging data in the raw-data domain by performing motion correction on at least one of the plurality of data sets based on the original TOF information and at least one corresponding MVF of the plurality of MVFs. The one or more processors may generate one or more target images of the object by performing, based on the corrected imaging data, image reconstruction.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 11 is a flowchart illustrating an exemplary process for generating corrected imaging data according to some embodiments of the present disclosure;

FIG. 12 is a schematic diagram illustrating exemplary rigid approximation performed on an original LOR section according to some embodiments of the present disclosure;

FIG. 13 is a schematic diagram illustrating exemplary transformed LOR sections according to some embodiments of the present disclosure;

FIG. 14 is a flowchart illustrating an exemplary process for generating one or more target images based on corrected imaging data according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 3:
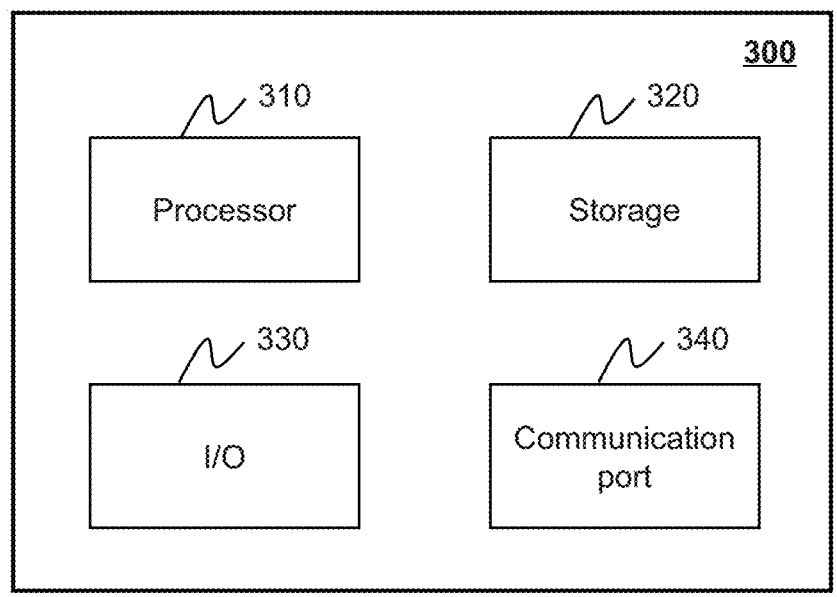
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The motion (e.g., rigid motion or non-rigid motion such as respiration motion) of a patient during a PET scan is responsible for motion blurring and mismatch artifacts in the resultant image. Therefore, motion compensation (also referred to as "motion correction") may be applied to reduce or eliminate motion blurring and mismatch artifacts in the resultant image. However, if a motion compensation method causes a dramatic increase of scan time and/or reconstruction time, it is undesirable for routine use and it can be challenging to combine motion compensation with other applications such as dynamic imaging.

The present disclosure provides a non-rigid motion compensation approach that is directly applied to original imaging data in a non-image domain, e.g., listmode or sinogram data. The original imaging data in a non-image domain may be acquired without going through image reconstruction, thereby saving processing time and/or computational resources. Due to the motion blur effect of non-rigid motion, an effective line of response (LOR) of a straight original LOR may become a non-straight line (e.g., a curved line or a broken line). With time of flight (TOF) information, the straight original LOR may be divided into a plurality of original LOR sections each of which corresponds to one of coincidence events of the original LOR. Rigid transformation may be performed on the original LOR sections to approximate the effective LOR, so as to achieve non-rigid motion compensation.

The following description is provided to help better understanding systems and/or methods for non-rigid motion correction in PET imaging. This is not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
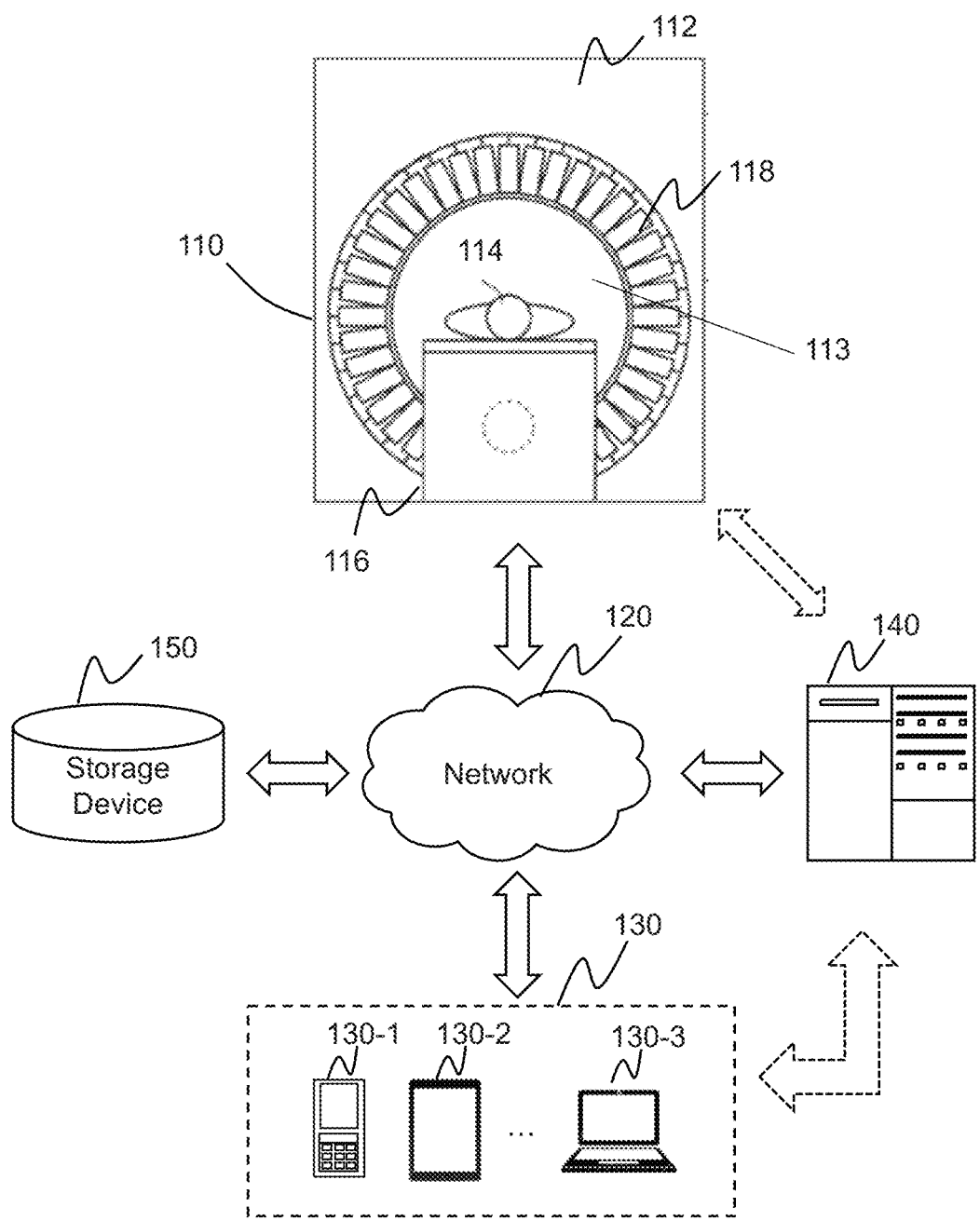
FIG. 1 is a schematic diagram illustrating an exemplary positron emission tomography (PET) system according to some embodiments of the present disclosure.

FIG. 1 is a schematic diagram illustrating an exemplary positron emission tomography (PET) system according to some embodiments of the present disclosure. PET imaging is based on coincidence events corresponding to detected photons arising from positron-electron annihilation.

The PET system 100 may include a PET scanner 110, a network 120, a terminal 130, a processing device 140, and a storage device 150. The components in the PET system 100 may be connected in one or more of various manners. Merely by way of example, the PET scanner 110 may be connected to the processing device 140 through the network 120. As another example, the PET scanner 110 may be connected to the processing device 140 directly (shown as the bi-directional arrow in dotted line linking the PET scanner 110 and the processing device 140). As another example, the processing device 140 may be connected to the storage device 150 through the network 120 or directly. As a further example, the processing device 140 may be connected to a terminal device (e.g., 130-1, 130-2, 130-3, etc.) through the network 120. As still a further example, the processing device 140 may be connected to a terminal device (e.g., 130-1, 130-2, 130-3, etc.) directly (shown as the bi-directional arrow in dotted line linking the terminal 130 and the processing device 140).

The PET scanner 110 may include a gantry 112, a table 116, and a detector 118. An object 114 injected with a substance (e.g., generally necessary for the metabolism of biological life, such as glucose, protein, nucleic acids, fatty acids, etc.) labeled with a tracer for the imaging purposes may be placed on the table 116. The detector 118 may be mounted on the gantry 112. The gantry 112 may form a detection channel 113.

The tracer refers to a radioactive substance (e.g., radionuclides such as 18F, 11C, etc.) that decays and emits positrons. The object 114 may be biological or non-biological. Merely by way of example, the object 114 may include a patient, a man-made object, etc. As another example, the object 114 may include a specific portion, organ, and/or tissue of the patient. For example, the object 114 may include the head, the brain, the neck, the body, a shoulder, an arm, the thorax, the heart, the stomach, a blood vessel, a soft tissue, a knee, a foot, or the like, of a patient, or any combination thereof.

Figure 2:
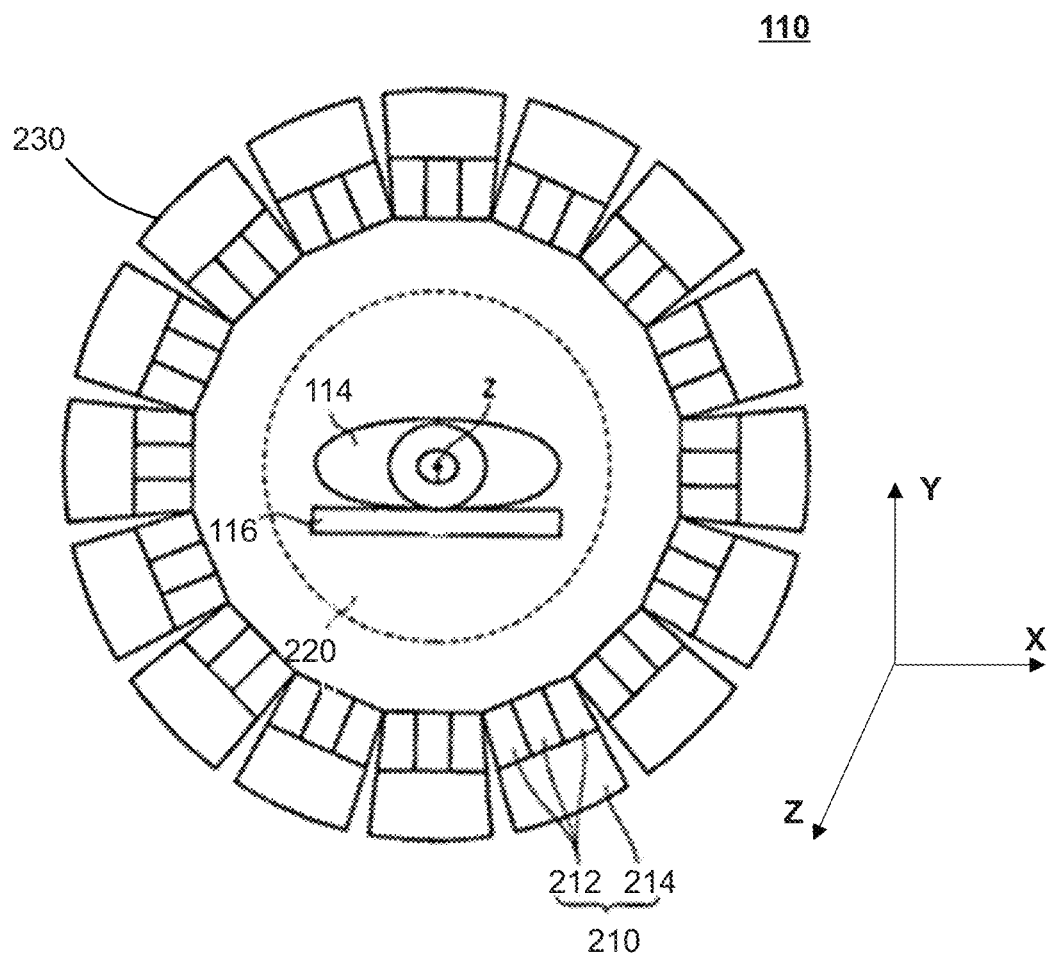
FIG. 2 is a cross section of an exemplary PET scanner according to some embodiments of the present disclosure.

In the present disclosure, the X axis, the Y axis, and the Z axis shown in FIG. 2 may form an orthogonal coordinate system. The X axis and the Z axis shown in FIG. 2 may be horizontal, and the Y axis may be vertical. As illustrated, the positive X direction along the X axis may be from the left side to the right side of the PET scanner 110 seen from the direction facing the front of the PET scanner 110; the positive Y direction along the Y axis shown in FIG. 2 may be from the lower part to the upper part of the PET scanner 110; the positive Z direction along the Z axis shown in FIG. 2 may refer to a direction in which the object is moved out of the detection channel 113 (or referred to as a bore) of the PET scanner 110.

As shown in FIG. 2, the detector 118 may include a plurality of detector rings (e.g., a detector ring 230) arranged along the Z direction (perpendicular to the paper as shown in FIG. 2). The plurality of detector rings may be located around the detection channel. A detector ring may include a plurality of detector units (e.g., a detector unit 210) arranged along the circumference of the detector ring.

The detector 118 may form a bore to accommodate the table 116. There may be afield of view (FOV) 220 in the bore. During a scan process, the object 114 along with the table 116 may be moved into the bore to position a region of interest (ROI) of the object 114 in the FOV 220.

As shown in FIG. 2, a detector unit 210 may include a scintillator 212 and a photodetector 214. The photodetector 214 may be operably coupled to the scintillator 212. In some embodiments, the scintillator 212 may include an array of scintillation crystals.

In some embodiments, positrons emitted from the radiation may travel through the object 114 until they encounter electrons. When a positron and an electron meet, annihilation may occur. The electron-positron annihilation may simultaneously generate two photons (e.g., 511-kiloelectron volt (keV) gamma photons) traveling in opposite directions along a line. The two photons may be detected by a pair of oppositely disposed detector units.

Each of the two photon generated by an electron-positron annihilation may strike the scintillator 212 to produce a burst of fluorescent light. The fluorescence may transmit from the scintillator 212 to the photodetector 214. The fluorescence may be converted to an electrical signal (e.g., an electrical pulse) by the photodetector 214. The electrical signal may be transmitted to other components of the PET system 100, such as the processing device 140, to be determined as a coincidence event. A straight line connecting the two detector units that detect the coincidence event may be referred to as an original line of response (LOR).

In some embodiments, the detector unit 210 may further include a light guide (not shown in FIG. 2) configured to provide a light path to the photodetector 214. In some embodiments, a front-end circuit board (not shown in FIG. 2) may be coupled to the photodetector 214 to process electrical signals and/or transmit electrical signals to other components (e.g., the processing device 140) of the PET system 100.

The network 120 may facilitate exchange of information and/or data. In some embodiments, one or more components in the PET system 100 (e.g., the PET scanner 110, the terminal 130, the processing device 140, or the storage device 150) may send information and/or data to other component(s) in the PET system 100 via the network 120. For example, the processing device 140 may obtain electrical signals from the PET scanner 110 via the network 120. As another example, the processing device 140 may obtain user instructions from the terminal 130 via the network 120. In some embodiments, the network 120 may be any type of wired or wireless network, or combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In some embodiments, the network 120 may include one or more network access points. For example, the network 120 may include wired or wireless network access points such as base stations and/or internet exchange points through which one or more components of the PET system 100 may be connected to the network 120 to exchange data and/or information.

The terminal 130 may include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. The terminal 130 may remotely operate the PET scanner 110. In some embodiments, the terminal 130 may operate the PET scanner 110 via a wireless connection. In some embodiments, the terminal 130 may receive information and/or instructions inputted by a user, and transmit the received information and/or instructions to the PET scanner 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

The processing device 140 may process data and/or information obtained from the PET scanner 110, the terminal 130, or the storage device 150. For example, the processing device 140 may obtain original imaging data of an object that is acquired from the PET scanner 110. The processing device 140 may generate corrected imaging data by performing non-rigid motion correction on the original imaging data. The processing device 140 may reconstruct an image of the object based on the corrected imaging data. In some embodiments, the processing device 140 may be a single server, or a server group. The server group may be centralized, or distributed. In some embodiments, the processing device 140 may be local or remote. For example, the processing device 140 may access information and/or data stored in the PET scanner 110, the terminal 130, and/or the storage device 150 via the network 120. As another example, the processing device 140 may be directly connected to the PET scanner 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 300 having one or more components illustrated in FIG. 3 in the present disclosure.

The storage device 150 may store data and/or instructions. In some embodiments, the storage device 150 may store data obtained from the terminal 130 and/or the processing device 140. For example, the storage device 150 may store images generated by the processing device 140. In some embodiments, the storage device 150 may store data and/or instructions that the processing device 140 may execute or use to perform exemplary methods described in the present disclosure. For example, the storage device 150 may store instructions that the processing device 140 may execute or use to generate corrected imaging data by performing non-rigid motion correction on original imaging data of an object and reconstruct an image of the object based on the corrected imaging data. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components in the PET system 100 (e.g., the processing device 140, the terminal 130). One or more components of the PET system 100 may access the data or instructions stored in the storage device 150 via the network 120. In some embodiments, the storage device 150 may be directly connected to or communicate with one or more components in the PET system 100 (e.g., the processing device 140, the terminal 130). In some embodiments, the storage device 150 may be part of the processing device 140.

FIG. 3 is a schematic diagram illustrating exemplary hardware and/or software components of a computing device on which the processing device 140 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 310 may process data obtained from the PET scanner 110, the terminal 130, the storage device 150, or any other component of the PET system 100. Specifically, the processor 310 may generate corrected imaging data by performing non-rigid motion correction on original imaging data of an object and reconstruct an image of the object based on the corrected imaging data. In some embodiments, the processor 310 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 300. However, it should be note that the computing device 300 in the present disclosure may also include multiple processors, thus operations and/or method steps that are performed by one processor as described in the present disclosure may also be jointly or separately performed by the multiple processors. For example, if in the present disclosure the processor of the computing device 300 executes both step A and step B, it should be understood that step A and step B may also be performed by two different processors jointly or separately in the computing device 300 (e.g., a first processor executes step A and a second processor executes step B, or the first and second processors jointly execute steps A and B).

The storage 320 may store data/information obtained from the PET scanner 110, the terminal 130, the storage device 150, or any other component of the PET system 100. In some embodiments, the storage 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 140 for generating corrected imaging data by performing non-rigid motion correction on original imaging data of an object and reconstructing an image of the object based on the corrected imaging data.

The I/O 330 may input or output signals, data, or information. In some embodiments, the I/O 330 may enable a user interaction with the processing device 140. For example, the processing device may display an image through the I/O 330. In some embodiments, the I/O 330 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 340 may be connected to a network (e.g., the network 120) to facilitate data communications. The communication port 340 may establish connections between the processing device 140 and the PET scanner 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
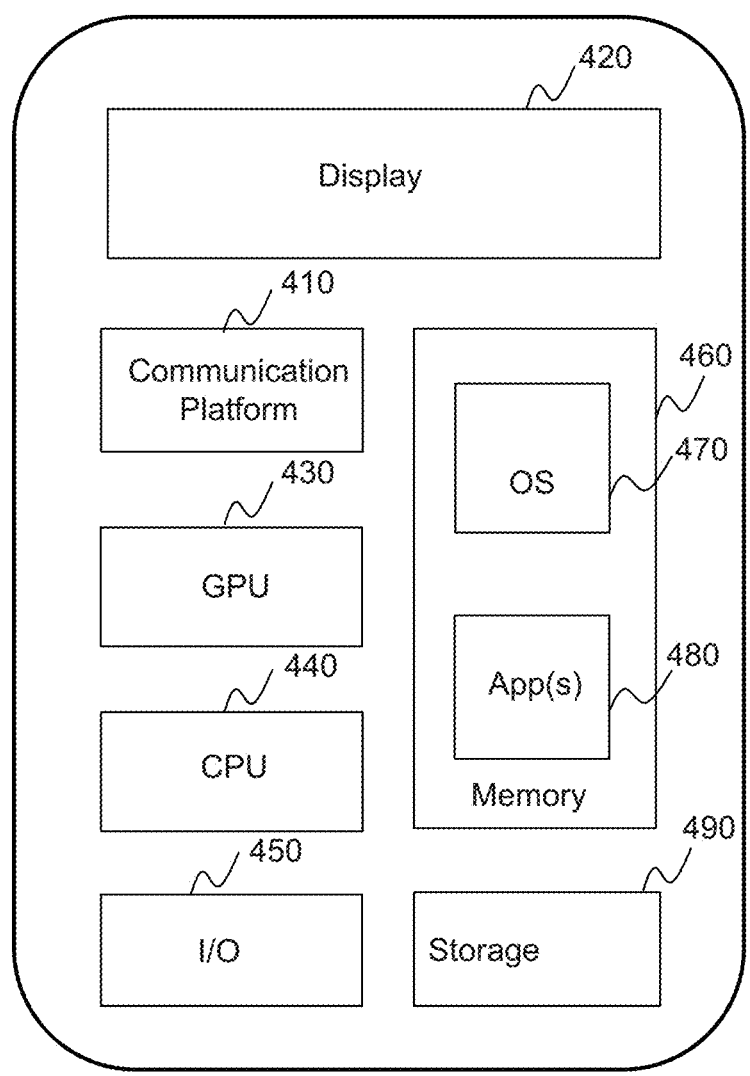
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device on which the terminal 130 may be implemented according to some embodiments of the present disclosure. As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS, Android, Windows Phone, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 140. User interactions with the information stream may be achieved via the I/O 450 and provided to the processing device 140 and/or other components of the PET system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 5:
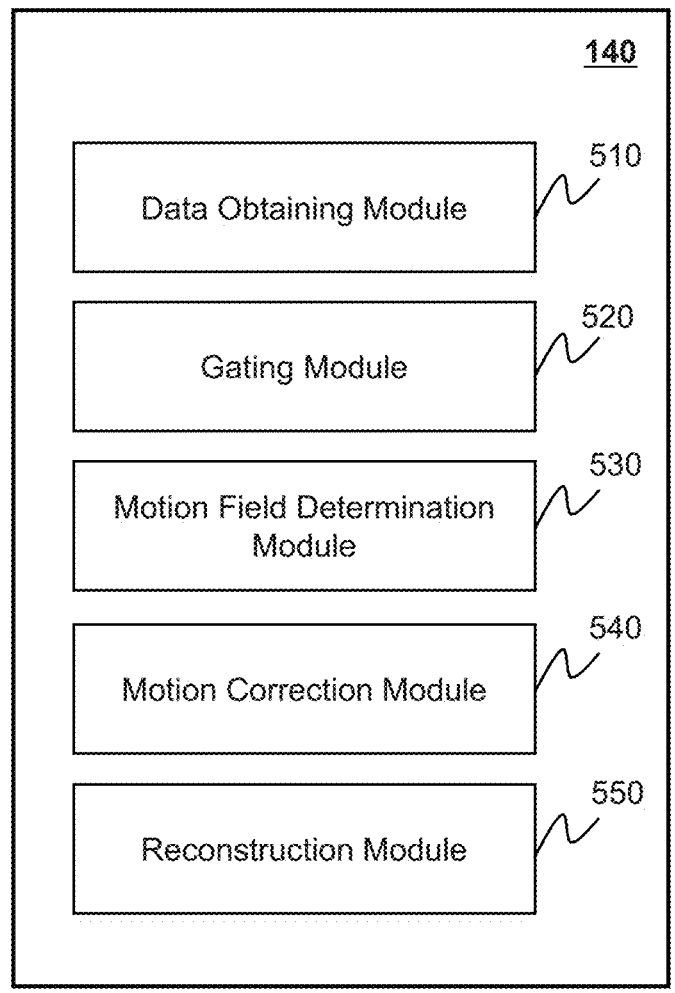
FIG. 5 is a block diagram illustrating an exemplary processing device according to some embodiments of the present disclosure.

FIG. 5 is a block diagram illustrating an exemplary processing device according to some embodiments of the present disclosure. The processing device 140 may include a data obtaining module 510, a gating module 520, a motion field determination module 530, a motion correction module 540, and a reconstruction module 550.

The data obtaining module 510 may be configured to obtain original imaging data of an object in a non-image domain (also referred to as a raw-data domain). The original imaging data may be subject to non-rigid motion of the object. The non-rigid motion may include physical motion such as respiration motion or cardiac motion, etc. In some embodiments, the original imaging data may be acquired by an imaging device (e.g., the PET scanner 110) within one or more motion cycles of the non-rigid motion.

In some embodiments, the original imaging data may include two-dimensional (2D) data or three-dimensional (3D) data. In some embodiments, the original imaging data may be recorded by measurement (e.g., respiratory gating, or cardiac gating) in time dimension.

The gating module 520 may be configured to gate the original imaging data into a plurality of data sets in the non-image domain each of which corresponds to a motion phase (e.g., end-inspiration (EI) or end-perspiration (EP) of respiration motion, or end-systole or end-diastole of cardiac motion) of a motion cycle of the non-rigid motion.

In gating, a motion cycle of the non-rigid motion may be divided into non-overlapping motion phase ranges each of which represents a motion phase in the motion cycle. Each detected emission corresponding to the same motion phase range may be assigned to one of the plurality of data sets, so that each of the plurality of data sets represents a part of the non-rigid motion cycle and is subjected to similar motion or location shift. In some embodiments, the gating may be performed with a surrogate motion signal representing the motion phase ranges. Any source or measure for acquiring the motion signal may be used, such as respiratory gating with a breathing sensor and/or a pressure sensor, cardiac gating with a cardiac motion sensor, a data-driven approach, etc.

The motion field determination module 530 may be configured to determine a plurality of motion vector fields (MVFs) based on the plurality of data sets. The plurality of motion vector fields may indicate the non-rigid motion. Each of the plurality of motion vector fields may correspond to one of the plurality of data sets and the corresponding motion phase. In some embodiments, a motion vector field (MVF) may include motion vectors each of which corresponds to a voxel in a region of interest (ROI) of the object. A motion vector of a voxel in the MVF may indicate a distance and a direction between a reference location of a reference voxel and the location of the voxel, in which the reference voxel and the voxel correspond to a same physical point, e.g., a same point in an ROI of an object.

Merely by way of example, assuming that the processing device 140 gates the original imaging data into N (N is integer and N≥2) data sets corresponding to N motion phases of a motion cycle of the non-rigid motion, an MVF estimation approach may be used.

The motion correction module 540 may be configured to generate corrected imaging data by performing motion correction (e.g., non-rigid motion correction) on at least one of the plurality of data sets based on at least one corresponding MVF of the plurality of motion vector fields and the original TOF information.

The motion (e.g., rigid motion or non-rigid motion such as respiration motion) of a patient during a PET scan may cause motion blurring and/or artifacts in the resultant image. Therefore, motion compensation (also referred to as "motion correction") may be applied to reduce or eliminate motion blurring and/or mismatch artifacts in the resultant image. However, if a motion compensation technique needs a dramatic increase of scan time and/or reconstruction time, it is undesirable for routine use and it can be challenging to combine motion compensation with other applications such as dynamic imaging.

An increase in the scan time and/or image reconstruction time of PET imaging to achieve motion correction may be avoided or reduced by performing motion correction directly on imaging data in a non-image domain (e.g., listmode data or sinogram data).

The motion of the object may cause a location shift of a straight original LOR, thereby leading to an effective LOR. In image reconstruction, the location where a coincident event occurs may be estimated according to the effective LORs, other than the original straight line LOR. The effective LOR needs to be determined before image reconstruction. One of the goals achieved by performing motion correction directly on imaging data in a non-image domain may be to estimate the effective LOR based on the original LOR before and obviating the need to perform image reconstruction at this stage of image data processing.

With the original TOF information, for a coincidence event, theoretically the annihilation position on the corresponding original LOR can be determined. However, because the time response of the PET system 100 has a certain error due to at least one factor including, e.g., the precision of the detector 118, the specific location of the annihilation position may be unknown based on the TOF information, instead, a certain range (also referred to as an original LOR section) within which the annihilation position is located may be determined. The range may be centered at a point. The range may depend on the temporal resolution of the PET system 100. The higher the temporal resolution is, the smaller the range may be. The position of the range on the original LOR may depend on the original TOF information of the coincidence event. Therefore, in TOF-PET reconstruction, for a coincidence event, it needs to estimate where in the original LOR section the coincidence event occurs, rather than the entire original LOR.

In some embodiments of the present disclosure, with the original TOF information, an original LOR may be divided into a plurality of original LOR sections each of which corresponds to one of coincidence events corresponding to the original LOR. The lengths of the plurality of original sections may depend on the temporal resolution of the PET system 100 and may be equal. The location of an original section on the original LOR may depend on the original TOF information of the corresponding coincidence event. In order to perform non-rigid motion correction directly on the original imaging data in a non-image domain, the processing device 140 may generate the corrected imaging data by performing rigid transformation on the original LOR sections to approximate the original LOR sections. The transformed LOR sections corresponding to original LOR sections of a same original LOR which is a straight line may form a non-straight effective LOR.

With the advance of the TOF technology, temporal resolution has reduced to 200 to 400 ps. An original LOR section, when compared with the entire original LOR, only covers a short length, compared to the entire original LOR. The much-reduced LOR length of the original LOR section makes curvature of the transformed LOR section of the effective LOR less significant, so that rigid transformation on the original LOR section on the basis of which a transformed LOR section is generated is expected to have a minimal impact on the approximation of the effective LOR. Details regarding generating the corrected imaging data can be found elsewhere in the present disclosure (e.g., descriptions in connection with FIG. 11).

The reconstruction module 550 may be configured to generate one or more target images of the object by performing, based on the corrected imaging data, image reconstruction. A regular reconstruction algorithm with minimal or no modifications can be applied based on the corrected imaging data to generate the one or more target images. Since the process for performing non-rigid motion correction to generate the corrected imaging data in the process 600 is fast, the time for image reconstruction with non-rigid motion compensation using the process 600 may be similar to the time for image reconstruction directly using the original imaging data without non-rigid motion compensation. Details regarding generating the one or more target images can be found elsewhere in the present disclosure (e.g., descriptions in connection with FIG. 14).

In some embodiments, the reconstruction module 550 may be further configured to generate a sensitivity map based on transformed detector locations corresponding to the coincidence events in the original imaging data. In some embodiments, the reconstruction module 550 may be further configured to generate one or more target images of an object based on the corrected imaging data and the sensitivity map.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided to two or more units. For example, the motion field determination module 530 and the motion correction module 540 may be combined as a single module configured to both determine a plurality of motion vector fields and perform non-rigid motion correction on the original imaging data. As another example, the reconstruction module 550 may be divided into two units. The first unit may be configured to determine an attenuation map. The second unit may be configured to generate an image based on the corrected imaging data and the attenuation map.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 5). The storage module may be configured to store data generated during any process performed by any component of in the processing device 140. As another example, each of components of the processing device 140 may include a storage apparatus. Additionally or alternatively, the components of the processing device 140 may share a common storage apparatus.

Figure 6:
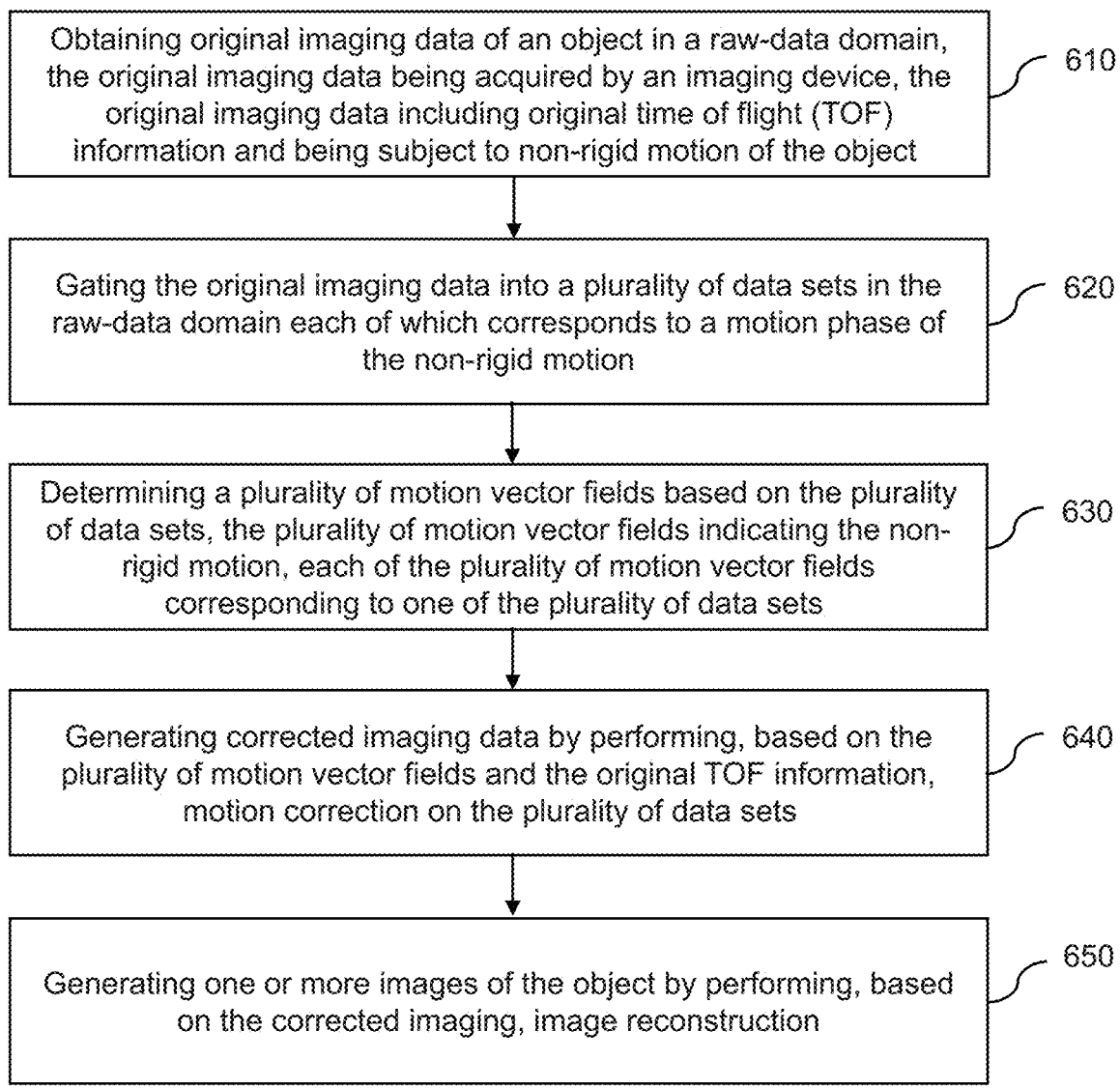
FIG. 6 is a flowchart illustrating an exemplary process for PET imaging according to some embodiments of the present disclosure.

FIG. 6 is a flowchart illustrating an exemplary process for PET imaging according to some embodiments of the present disclosure. The process 600 may be implemented in the PET system 100 illustrated in FIG. 1. For example, the process 600 may be stored in the storage device 150 and/or the storage 320 in the form of instructions (e.g., an application), and invoked and/or executed by the processing device 140 (e.g., the processor 310 illustrated in FIG. 3, or one or more modules in the processing device 140 illustrated in FIG. 5). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, the processing device 140 (e.g., the data obtaining module 510) may obtain original imaging data of an object in a non-image domain (also referred to as a raw-data domain). The original imaging data may be subject to non-rigid motion of the object. The non-rigid motion may include physical motion such as respiration motion or cardiac motion, etc. In some embodiments, the original imaging data may be acquired by an imaging device (e.g., the PET scanner 110) within one or more motion cycles of the non-rigid motion.

In some embodiments, the original imaging data may include event information of a plurality of coincidence events. For example, the event information of one of the plurality of coincidence events may include original detector locations of two detector units detecting the coincidence event, LOR information (e.g., the location, the length, etc.) of a straight original LOR corresponding to the coincidence event, original time of flight (TOF) information of the coincidence event, energy of two photons of the coincidence event, detection time when the coincidence event is detected, or the like, or any combination thereof. The original TOF information of the coincidence event may include a first TOF of a first photon of the coincidence event, a second TOF of a second photon of the coincidence event, a difference between the first TOF and the second TOF, or the like, or any combination thereof.

In some embodiments, the original imaging data in a non-image domain may represent the detected emissions by the detector 118. The original imaging data may be in listmode format or sinogram format. The original imaging data in listmode format may be referred to as listmode data. The original imaging data in sinogram format may be referred to as sinogram data. The original imaging data in a non-image domain may be acquired without going through image reconstruction, thereby saving processing time and/or computational resources.

In some embodiments, in the listmode data, information of a pair of detected photons corresponding to each coincidence event may be recorded and stored in a list format. For example, for a pair of detected photons of a coincidence event, information such as energy deposition locations of the two photons on the detector 118 (i.e., original detector locations of two detector units of the detector 118 detecting the two photons), energy of the two photons, and detection time of the two photons by the two detector units may be recorded and stored in a list format.

In some embodiments, in the sinogram data, an original LOR may be recorded and stored in a format of, e.g., (r, θ, ω).

Figures 7A, 7B:
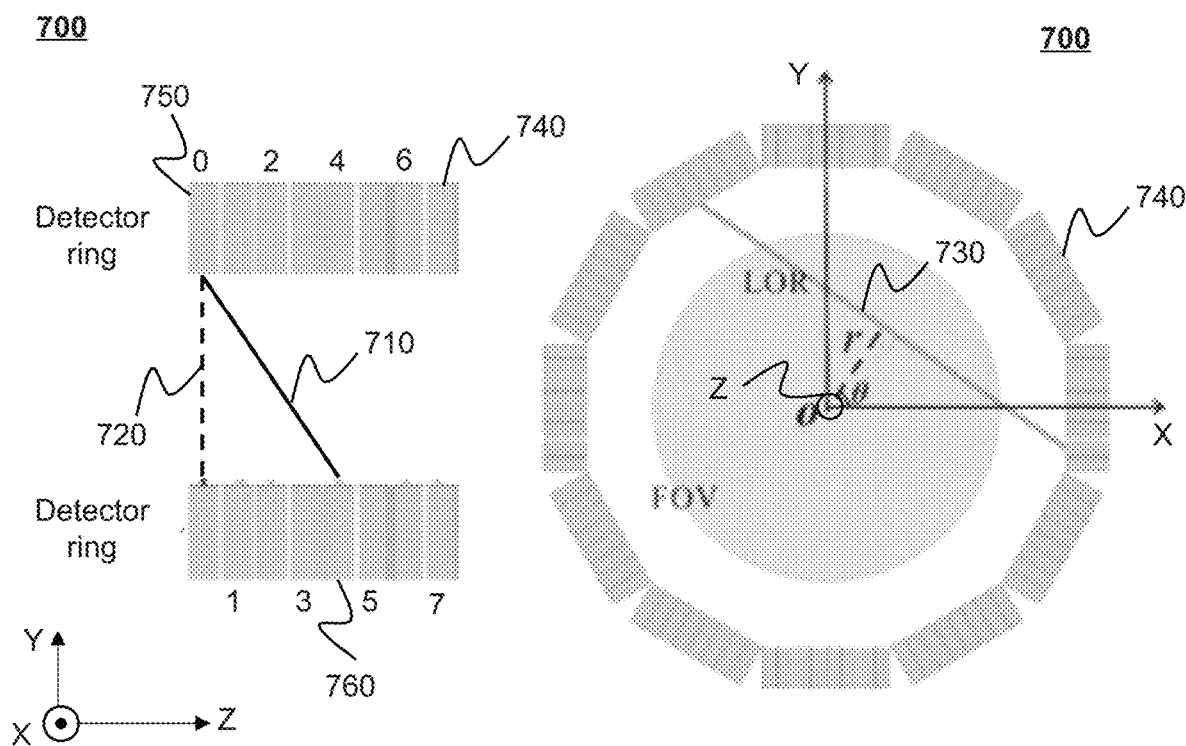
FIG. 7A is a schematic diagram illustrating a cross section of an exemplary configuration of a detector parallel to a Z direction according to some embodiments of the present disclosure.
FIG. 7B is a schematic diagram illustrating a cross section of the exemplary configuration of the detector in FIG. 7A perpendicular to the Z direction according to some embodiments of the present disclosure.

Merely by way of example, FIG. 7A is a schematic diagram illustrating a cross section of an exemplary configuration 700 of the detector 118 parallel to the Z direction according to some embodiments of the present disclosure. FIG. 7B is a schematic diagram illustrating a cross section of the exemplary configuration 700 of the detector 118 perpendicular to the Z direction according to some embodiments of the present disclosure. The X, Y, and Z directions in FIGS. 7A and 7B correspond to those in FIG. 1. In FIG. 7A, the positive X direction is perpendicular to the paper and points outward. In FIG. 7B, the positive Z direction is perpendicular to the paper and points outward.

According to the configuration 700 of the detector 118, the detector 118 includes 8 detector rings, each of which is assigned a serial number (e.g., 0-7) to represent locations of the 8 detector rings in the detector 118. For an original LOR, ω represents the location(s) (e.g., the serial number(s)) of the detector ring(s) of the detector 118 that the original LOR is located in or between.

As shown in FIG. 7B, the original LOR 730 is located in the detector ring 740 (e.g., the detector ring with the serial number "7" in FIG. 7A) of the detector 118. A distance between the center point O of the detector ring 740 and the original LOR 730 may be recorded as r. The angle between the perpendicular line from the center point O to the original LOR 730 and the X direction may be recorded as θ.

As shown in FIG. 7A, the original LOR 710 is located between the detector ring 750 (e.g., the detector ring with the serial number "0") and the detector ring 760 (e.g., the detector ring with the serial number "4") of the detector 118. The original LOR 710 may be first projected onto a target detector ring (e.g., the detector ring 750 or the detector ring 760) of the detector 118 along the Z direction, then r and θ of the original LOR 710 may be determined based on the projected LOR in the target detector ring. For example, as shown in FIG. 7A, the original LOR 710 may be first projected onto the detector ring 750 along the Z direction to obtain a projected LOR 720. Then r and θ of the original LOR 710 may be determined based on the projected LOR 720 in the detector ring 750.

In some embodiments, in the sinogram data without original TOF information, a coincidence event corresponding to an original LOR may be recorded as (r, θ, ω). In some embodiments, in the sinogram data with original TOF information, a coincidence event corresponding to an original LOR may be recorded as (r, θ, ω, τ), where τ refers to the original TOF information of the coincidence event. In some embodiments, the sinogram data may be obtained by transforming the listmode data.

In some embodiments, the original imaging data may include two-dimensional (2D) data or three-dimensional (3D) data. In some embodiments, the original imaging data may be recorded by measurement (e.g., respiratory gating, or cardiac gating) in time dimension.

In 620, the processing device 140 (e.g., the gating module 520) may gate the original imaging data into a plurality of data sets in the non-image domain each of which corresponds to a motion phase (e.g., end-inspiration (EI) or end-perspiration (EP) of respiration motion, or end-systole or end-diastole of cardiac motion) of a motion cycle of the non-rigid motion.

In gating, a motion cycle of the non-rigid motion may be divided into non-overlapping motion phase ranges each of which represents a motion phase in the motion cycle. Each detected emission corresponding to the same motion phase range may be assigned to one of the plurality of data sets, so that each of the plurality of data sets represents a part of the non-rigid motion cycle and is subjected to similar motion or location shift. In some embodiments, the gating may be performed with a surrogate motion signal representing the motion phase ranges. Any source or measure for acquiring the motion signal may be used, such as respiratory gating with a breathing sensor and/or a pressure sensor, cardiac gating with a cardiac motion sensor, a data-driven approach, etc.

In 630, the processing device 140 (e.g., the motion field determination module 530) may determine a plurality of motion vector fields (MVFs) based on the plurality of data sets. The plurality of motion vector fields may indicate the non-rigid motion. Each of the plurality of motion vector fields may correspond to one of the plurality of data sets and the corresponding motion phase. In some embodiments, a motion vector field (MVF) may include motion vectors each of which corresponds to a voxel in a region of interest (ROI) of the object. A motion vector of a voxel in the MVF may indicate a distance and a direction between a reference location of a reference voxel and the location of the voxel, in which the reference voxel and the voxel correspond to a same physical point, e.g., a same point in an ROI of an object.

Merely by way of example, assuming that the processing device 140 gates the original imaging data into N (N is integer and N≥2) data sets corresponding to N motion phases of a motion cycle of the non-rigid motion, an MVF estimation approach may be used.

The processing device 140 may obtain at least two intermediate images by performing reconstruction on at least two of the N data sets. The processing device 140 may select one of the at least two intermediate images as a reference image. For example, the processing device 140 may select, as the reference image, the intermediate image corresponding to maximum magnitude (e.g., end-inspiration (EI) or end-perspiration (EP) of respiration motion, or end-systole or end-diastole of cardiac motion) among the at least two motion phases. The processing device 140 may perform registration on the other intermediate images based on the reference image. The processing device 140 may obtain N motion vector fields based on the reference image, the N data sets, and the other intermediate images.

For example, the processing device 140 may obtain N intermediate images by performing reconstruction on the N data sets. The processing device 140 may select one of the N intermediate images as a reference image. For example, the processing device 140 may select, as the reference image, the intermediate image corresponding to maximum magnitude (e.g., end-inspiration (EI) or end-perspiration (EP) of respiration motion, or end-systole or end-diastole of cardiac motion) among the N motion phases. The processing device 140 may perform registration on the other N−1 intermediate images based on the reference image. For example, the processing device 140 may perform registration between each of the other N−1 intermediate image and the reference image. The processing device 140 may obtain motion vector fields of the N motion phases by comparing each of the other N−1 registration intermediate image and the reference image.

As another example, the processing device 140 may select M (M is an integer, and 2≤M<N) of the N data sets that correspond to M motion phases (e.g., end-inspiration (EI) and end-perspiration (EP) of respiration motion, or end-systole and end-diastole of cardiac motion) a difference between the motion magnitudes of which exceeds a threshold. For example, the processing device 140 may select 2 data sets that correspond to EI and EP of respiration motion. As another example, the processing device 140 may select M (M>2) data sets that correspond to EI, EP, and one or more motion phases between EI and EP. The processing device 140 may obtain M intermediate images by performing reconstruction on the M data sets. The processing device 140 may select one of the M intermediate images as a reference image. For example, the processing device 140 may select, as the reference image, the intermediate image corresponding to the maximum motion magnitude among the M motion phases. The processing device 140 may perform registration between each of the other M−1 intermediate images and the reference image. The processing device 140 may obtain M−1 motion vector fields from the other M−1 intermediate images by comparing each of the other M−1 intermediate images with the reference image. The processing device 140 may obtain the motion vector fields of any N motion phases by performing interpolation based on the reference image, the M−1 motion vector fields determined from the other M−1 intermediate images, and the N data sets.

In some embodiments, the processing device 140 may generate the intermediate images with the original TOF information. In some embodiments, to reduce the computational cost, the processing device 140 may generate the intermediate images without the original TOF information. In some embodiments, the processing device 140 may generate the intermediate images without motion correction.

In some embodiments, in the motion compensation, MVF estimation may be time-consuming. Since the MVF estimation doesn't need quantitatively accurate reconstruction, approximations such as reconstruction with less accurate modeling, or filtered back projection (FBP) reconstruction, or the TOF histoimage may be used to generate the intermediate images so as to accelerate MVF estimation. For example, the use of a back projection algorithm to generate two intermediate images may allow a more accelerated MVF estimation, thereby in turn reducing the processing time by avoid image reconstruction.

In 640, the processing device 140 (e.g., the motion correction module 540) may generate corrected imaging data by performing motion correction (e.g., non-rigid motion correction) on at least one of the plurality of data sets based on at least one corresponding MVF of the plurality of motion vector fields and the original TOF information.

The motion (e.g., rigid motion or non-rigid motion such as respiration motion) of a patient during a PET scan may cause motion blurring and/or artifacts in the resultant image. Therefore, motion compensation (also referred to as "motion correction") may be applied to reduce or eliminate motion blurring and/or mismatch artifacts in the resultant image. However, if a motion compensation technique needs a dramatic increase of scan time and/or reconstruction time, it is undesirable for routine use and it can be challenging to combine motion compensation with other applications such as dynamic imaging.

An increase in the scan time and/or image reconstruction time of PET imaging to achieve motion correction may be avoided or reduced by performing motion correction directly on imaging data in a non-image domain (e.g., listmode data or sinogram data).

The motion of the object may cause a location shift of a straight original LOR, thereby leading to an effective LOR. In image reconstruction, the location where a coincident event occurs may be estimated according to the effective LORs, other than the original straight line LOR. The effective LOR needs to be determined before image reconstruction. One of the goals achieved by performing motion correction directly on imaging data in a non-image domain may be to estimate the effective LOR based on the original LOR before and obviating the need to perform image reconstruction at this stage of image data processing.

Figure 8:
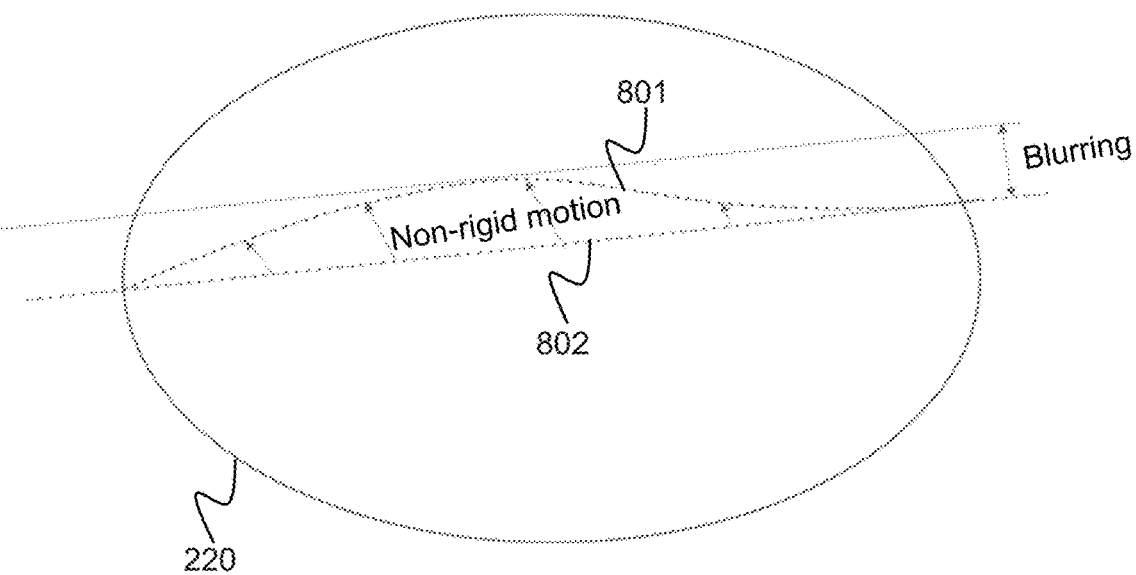
FIG. 8 is a schematic diagram illustrating an exemplary effective LOR according to some embodiments of the present disclosure.

As for rigid motion, the effective LOR of a straight original LOR is still a straight line. Rigid motion correction can be directly applied to imaging data in a non-image domain by performing rigid transformation on the entire original LOR to estimate the effective LOR. However, as shown in FIG. 8, due to the motion blur effect of non-rigid motion, the effective LOR 801 of the original LOR 802 in the FOV 220 of the PET scanner 110 becomes a non-straight line (e.g., a curved line). If the original LOR 802 was used directly for reconstruction, a blurring effect may be produced in the reconstructed image so determined.

Figure 9:
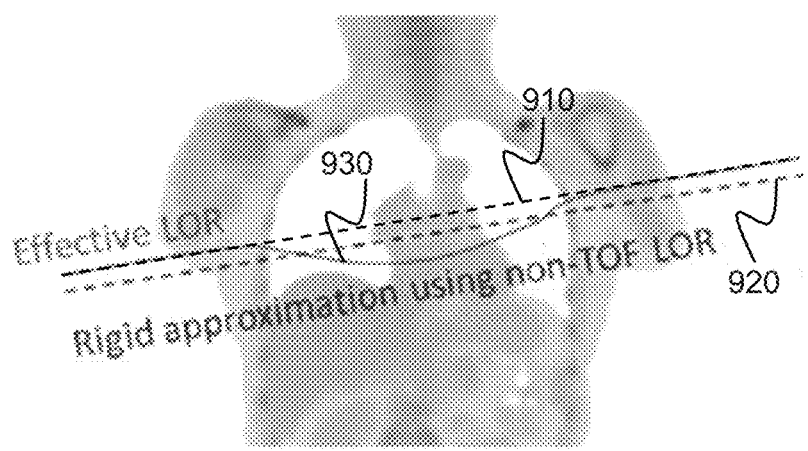
FIG. 9 is a schematic diagram illustrating exemplary rigid approximation using non-time-of-flight (TOF) LOR according to some embodiments of the present disclosure.

Without the original TOF information, during image reconstruction, it is assumed that the probability of a coincidence event occurring at all positions on the corresponding original LOR is the same, that is, the contribution of each point on the original LOR is the same. Without the original TOF information, rigid transformation (also referred to as rigid approximation) may be applied only to the entire original LOR. As shown in FIG. 9, due to the motion blur effect of non-rigid motion, the effective LOR 930 of the original LOR 910 becomes a non-straight line (e.g., a curved line). A straight LOR 920 is obtained by performing rigid transformation on the entire original LOR 910. It can be seen that a significant error is still present between the LOR 920 and the effective LOR 930, which is inappropriate for non-rigid motion correction.

With the original TOF information, for a coincidence event, theoretically the annihilation position on the corresponding original LOR can be determined. However, because the time response of the PET system 100 has a certain error due to at least one factor including, e.g., the precision of the detector 118, the specific location of the annihilation position may be unknown based on the TOF information, instead, a certain range (also referred to as an original LOR section) within which the annihilation position is located may be determined. The range may be centered at a point. The range may depend on the temporal resolution of the PET system 100. The higher the temporal resolution is, the smaller the range may be. The position of the range on the original LOR may depend on the original TOF information of the coincidence event. Therefore, in TOF-PET reconstruction, for a coincidence event, it needs to estimate where in the original LOR section the coincidence event occurs, rather than the entire original LOR.

Figure 10:
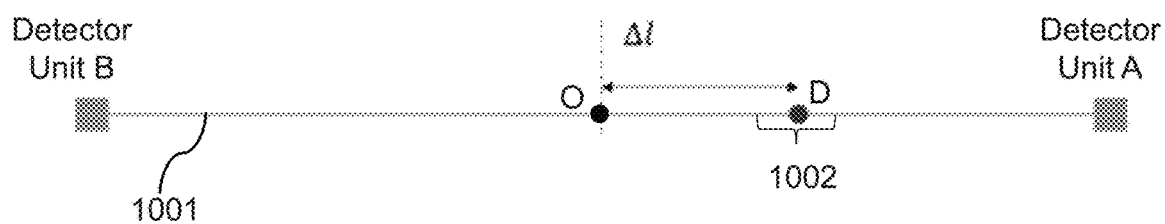
FIG. 10 is a schematic diagram illustrating an exemplary original LOR section according to some embodiments of the present disclosure.

For example, FIG. 10 is a schematic diagram illustrating an exemplary original LOR according to some embodiments of the present disclosure. As shown in FIG. 10, the straight line 1001 may be an original LOR connecting detector unit A and detector unit B of the detector 118. Theoretically, the annihilation position D of a coincidence event on the original LOR 1001 can be determined based on Equation (1) below:

$$\Delta l = \frac{T_B - T_A}{2} c, \quad (1)$$

where Δl refers to a distance from the center O of the LOR 1001 to the position D, $T_A$ refers to the TOF of a first photon of the coincidence event detected by the detector unit A, and $T_B$ refers to the TOF of a second photon of the coincidence event detected by the detector unit B, and c refers to the speed of light. However, because the time response of the PET system 100 has a certain error, a certain range 1002 (also referred to as an original LOR section) centered on a point within which the annihilation occurs, but not a specific position of the annihilation, may be determined based on Equation (1).

In some embodiments of the present disclosure, with the original TOF information, an original LOR may be divided into a plurality of original LOR sections each of which corresponds to one of coincidence events corresponding to the original LOR. The lengths of the plurality of original sections may depend on the temporal resolution of the PET system 100 and may be equal. The location of an original section on the original LOR may depend on the original TOF information of the corresponding coincidence event. In order to perform non-rigid motion correction directly on the original imaging data in a non-image domain, the processing device 140 may generate the corrected imaging data by performing rigid transformation on the original LOR sections to approximate the original LOR sections. The transformed LOR sections corresponding to original LOR sections of a same original LOR which is a straight line may form a non-straight effective LOR.

With the advance of the TOF technology, temporal resolution has reduced to 200 to 400 ps. An original LOR section, when compared with the entire original LOR, only covers a short length, compared to the entire original LOR. The much-reduced LOR length of the original LOR section makes curvature of the transformed LOR section of the effective LOR less significant, so that rigid transformation on the original LOR section on the basis of which a transformed LOR section is generated is expected to have a minimal impact on the approximation of the effective LOR. Details regarding generating the corrected imaging data can be found elsewhere in the present disclosure (e.g., descriptions in connection with FIG. 11).

In 650, the processing device 140 (e.g., the reconstruction module 550) may generate one or more target images of the object by performing, based on the corrected imaging data, image reconstruction. A regular reconstruction algorithm with minimal or no modifications can be applied based on the corrected imaging data to generate the one or more target images. Since the process for performing non-rigid motion correction to generate the corrected imaging data in the process 600 is fast, the time for image reconstruction with non-rigid motion compensation using the process 600 may be similar to the time for image reconstruction directly using the original imaging data without non-rigid motion compensation. Details regarding generating the one or more target images can be found elsewhere in the present disclosure (e.g., descriptions in connection with FIG. 14).

In some embodiments, the process 600 may be applied in 2D PET imaging, 3D PET imaging, or dynamic PET imaging. For example, the processing device 140 may generate a plurality of target images of an object based on the process 600. The plurality of target images may indicate respiration motion of the object in one or more respiration cycles.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 11 is a flowchart illustrating an exemplary process for generating corrected imaging data according to some embodiments of the present disclosure. The process 1100 may be implemented in the PET system 100 illustrated in FIG. 1. For example, the process 1100 may be stored in the storage device 150 and/or the storage 320 in the form of instructions (e.g., an application), and invoked and/or executed by the processing device 140 (e.g., the processor 310 illustrated in FIG. 3, or one or more modules in the processing device 140 illustrated in FIG. 5). The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting. In some embodiments, the processing device 140 may perform operation 640 of the process 600 in FIG. 6 based on the process 1100.

For brevity, in the process 1100, an original LOR of one of the plurality of data sets are taken as an example. The processing device 140 may process any original LOR of the plurality of data sets based on the process 1100.

In 1110, for each of a plurality of original LOR sections of an original LOR of a data set, the processing device 140 (e.g., the motion correction module 540) may determine a transformed LOR section by performing, based on a motion vector field corresponding to the data set, rigid transformation on the original LOR section. In some embodiments, the transformed LOR sections may be straight lines.

One of the plurality of original LOR sections may be taken as an example. In some embodiments, the processing device 140 may identify, in the MVF, target motion vectors of voxels of the object corresponding to the original LOR section. The processing device 140 may obtain the transformed LOR section by performing, based on the target motion vectors, rigid transformation on the original LOR section. The rigid transformation on the original LOR section may be referred to as non-deformable transformation (e.g., translation and/or rotation) on the original LOR section.

For example, the processing device 140 may identify, in the MVF, at least two target motion vectors of voxels of the object, in which each of the at least two target motion vectors may correspond to a point of the original LOR section. The processing device 140 may determine a rigid transformation function by fitting the at least two target motion vectors. The processing device 140 may obtain the transformed LOR section by performing, based on the rigid transformation function, rigid transformation on the original LOR section.

In 1120, the processing device 140 (e.g., the motion correction module 540) may determine transformed TOF information corresponding to the transformed LOR section by performing, based on the motion vector field corresponding to the data set, the rigid transformation on original TOF information of the original LOR section. In some embodiments, the transformed TOF information corresponding to the transformed LOR section may include two transformed TOFs corresponding to the transformed LOR section and/or a difference between the two transformed TOFs.

For example, the processing device 140 may determine the location of the center point of the transformed LOR section. The processing device 140 may determine a distance between the center point of the transformed LOR section and the center point of the LOR where the transformed LOR section is located. The processing device 140 may determine the transformed TOF information (e.g., a TOF difference) based on the distance using Equation (1).

As another example, the processing device 140 may transform the center point of the original LOR section based on the rigid transformation illustrated in operation 1110. The processing device 140 may transform the center point of the original LOR based on the rigid transformation illustrated in operation 1110. The processing device 140 may determine a distance between the transformed center point of the original LOR section and the transformed center point of the original LOR. The processing device 140 may determine the transformed TOF information (e.g., a TOF difference) based on the distance using Equation (1).

In 1130, the processing device 140 (e.g., the motion correction module 540) may determine, based on the motion vector field corresponding to the data set and the rigid transformation on original detector locations of two first detector units, transformed detector locations of two second detector locations. The two first detector units may be two of the plurality of detector units of the detector 118 and correspond to the original LOR. The two second detector units may be two of the plurality of detector units of the detector 118 and correspond to the transformed LOR section. In some embodiments, the processing device 140 may determine the transformed detector locations by performing the rigid transformation illustrated in operation 1110 on the original detector locations.

In 1140, the processing device 140 (e.g., the motion correction module 540) may generate corrected imaging data based on at least one of the transformed LOR sections, the transformed TOF information corresponding to the transformed LOR sections, or the transformed detector locations corresponding to the transformed LOR sections.

In some embodiments, according to operations 1110-1130, the original coordinates of a coincidence event may be transformed from a set corresponding to the original LOR section, the original TOF information, and the original detector locations to a set corresponding to the transformed LOR section, the transformed TOF information, and the transformed detector locations. The processing device 140 may generate the corrected imaging data by substituting the original coordinates of coincident events with the transformed coordinates of the coincidence events.

FIG. 12 is a schematic diagram illustrating an exemplary rigid transformation of an original LOR section according to some embodiments of the present disclosure. In the example of FIG. 12, the original imaging data is sinogram data. An original LOR 1204 may be represented as $(r_1, \theta_1)$. An original LOR section 1202 of the original LOR 1204 corresponding a coincidence event may be represented as $(r_1, \theta_1, \tau_1)$, where $\tau_1$ refers to the original TOF information of the coincidence event. The original LOR section 1202 (and the original LOR 1204) corresponds to detector units C and D of the detector 118. The original detector locations of the detector units C and D may be represented as $(C_x, C_y, C_z)$ and $(D_x, D_y, D_z)$, where $C_x$, $C_y$, and $C_z$ refer to the coordinates of the detector unit C in the coordinate system illustrated in FIG. 1, and $D_x$, $D_y$, and $D_z$ refer to the coordinates of the detector unit D in the coordinate system illustrated in FIG. 1. The original coordinates of the coincidence event in the original imaging data may be represented as $\{(r_1, \theta_1, \tau_1), (C_x, C_y, C_z), (D_x, D_y, D_z)\}$.

By performing the rigid transformation illustrated in the process 1100 on the original LOR section 1202, the original LOR section 1202 may be transformed to a transformed LOR section 1203 represented as $(r_2, \theta_2, \tau_2)$, where $\tau_2$ refers to the transformed TOF information corresponding to the transformed LOR section 1203. The transformed LOR section 1203 corresponds to detector units C' and D' of the detector 118. The transformed detector locations of the detector units C' and D' may be represented as $(C'_x, C'_y, C'_z)$ and $(D'_x, D'_y, D'_z)$, where $C'_x$, $C'_y$, and $C'_z$ refer to the coordinates of the detector unit C' in the coordinate system illustrated in FIG. 1, and $D'_x$, $D'_y$, and $D'_z$ refer to the coordinates of the detector unit D' in the coordinate system illustrated in FIG. 1. The transformed coordinates of the coincidence event in the corrected imaging data may be represented as $\{(r_2, \theta_2, \tau_2), (C'_x, C'_y, C'_z), (D'_x, D'_y, D'_z)\}$.

FIG. 13 is a schematic diagram illustrating exemplary transformed LOR sections according to some embodiments of the present disclosure. As illustrated, the original LOR 1320 is divided into 7 original LOR sections. The processing device 140 may determine 7 transformed LOR sections (e.g., the 7 dashed straight lines such as 1310 in FIG. 13) by performing, based on the process 1100, rigid transformation on each of the original LOR sections. As shown in FIG. 13, the 7 straight transformed LOR sections approximate the effective LOR 1330 (the solid curved line 1330 in FIG. 13) with less error.

In some embodiments, a simplification may be applied in the rigid transformation. For example, the rotational transformation may be ignored in the rigid transformation, and the rigid transformation of an LOR section may be achieved by translating the corresponding original LOR section by a distance determined based on the motion vectors corresponding to two ends of the LOR section. As another example, the coincidence event corresponding to which the transformed LOR section is out of the FOV of the PET scanner 110 may be discarded.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, at least two of operations 1110-1130 may be performed simultaneously or in turn.

FIG. 14 is a flowchart illustrating an exemplary process for generating one or more target images based on corrected imaging data according to some embodiments of the present disclosure. The process 1400 may be implemented in the PET system 100 illustrated in FIG. 1. For example, the process 1400 may be stored in the storage device 150 and/or the storage 320 in the form of instructions (e.g., an application), and invoked and/or executed by the processing device 140 (e.g., the processor 310 illustrated in FIG. 3, or one or more modules in the processing device 140 illustrated in FIG. 5). The operations of the illustrated process presented below are intended to be illustrative. In some embodiments, the process 1400 may be accomplished with one or more additional operations not described, and/or without one or more of the operations discussed. Additionally, the order in which the operations of the process 1400 as illustrated in FIG. 14 and described below is not intended to be limiting. In some embodiments, the processing device 140 may perform operation 650 of the process 600 in FIG. 6 based on the process 1400.

In 1410, the processing device 140 (e.g., the reconstruction module 550) may generate a sensitivity map based on transformed detector locations corresponding to the coincidence events in the original imaging data. For example, the sensitivity map may be generated by transforming the detector locations, and modifying the corresponding detection possibility of those LORs that are affected by motion. In the corrected imaging data, a coincidence event may be deemed as being detected by two detector units located at the transformed detector locations. However, the coincidence event is actually detected by two detector units located at the original detector locations. The sensitivity map may be configured to correct the transformed detector locations in the corrected imaging data by. In the result of applying the sensitivity map in reconstruction of the corrected imaging data, the coincidence event in the corrected imaging data may be deemed as being detected by the original detector locations.

In 1420, the processing device 140 (e.g., the reconstruction module 550) may generate one or more target images of an object based on the corrected imaging data and the sensitivity map. In some embodiments, a regular reconstruction algorithm with minimal or no modifications can be applied to perform reconstruction on the corrected imaging data and the sensitivity map to generate the one or more target images. The regular reconstruction algorithm may include an FBP algorithm, an iterative reconstruction algorithm (e.g., ordered subsets expectation maximization (OSEM)), or the like, or any combination thereof.

For example, a regular reconstruction algorithm may be represented using Equation (2) below:

$$\lambda_i^{n+1} = \frac{\lambda_i^n}{\sum_j H_{i,j}} \sum_j H_{i,j} \frac{p_j}{\sum_i H_{i,j}\lambda_i^n + r_j}, \quad (2)$$

where $\lambda_i^n$ refers to an image value at voxel i of the object determined in the $n^{th}$ iteration of the regular reconstruction algorithm; $\lambda_i^{n+1}$ refers to an image value at voxel i determined in the $(n+1)^{th}$ iteration of the regular reconstruction algorithm; $p_j$ refers to an original LOR section j corresponding to voxel i; $H_{i,j}$ refers to a projection matrix corresponding to voxel i and original LOR section j; and $r_j$ refers to the scatter and random effects corresponding to original LOR section j.

In some embodiments, the processing device 140 may perform reconstruction on the corrected imaging data and the sensitivity map using Equation (3) below:

$$\lambda_i^{n+1} = \frac{\lambda_i^n}{\sum_j R_j H_{i,j}} \sum_j H_{i,j} \frac{p'_j}{\sum_i H_{i,j}\lambda_i^n + r_j}, \quad (3)$$

where $p'_j$ refers to a transformed LOR section corresponding to original LOR section j; and $R_j$ refers to the transformed detector locations corresponding to original LOR section j in the sensitivity map. A slight modification may be performed on the regular reconstruction algorithm of Equation (2) to achieve the reconstruction algorithm of Equation (3). The slight modification may include correcting detector locations in the correcting imaging data using the sensitivity map during reconstruction.

In some embodiments, the processing device 140 may perform reconstruction on the corrected imaging data and the sensitivity map using Equation (4) below:

$$\lambda_i^{n+1} = \frac{\lambda_i^n}{\sum_j H_{i,j}} \sum_j H_{i,j} \frac{p'_j/R_j}{\sum_i H_{i,j}\lambda_i^n + r_j}. \quad (4)$$

Before reconstruction, the processing device 140 may correct the detector locations in the corrected imaging data using the sensitivity map by applying the sensitivity map in the reconstruction of the corrected imaging data. With the result of $p'_j/R_j$ as the input, the regular reconstruction algorithm of Equation (2) without further modification may be used to generate the one or more target images.

In some embodiments, the processing device 140 may generate an attenuation map (e.g., a computed tomography (CT) image) using the plurality of MVFs based on any existing approach for generating an attenuation map. For example, the processing device 140 may obtain activity images (e.g., PET images generated based on the original imaging data) at different motion phases of the non-rigid motion using the plurality of MVFs. The processing device 140 may generate the attenuation map based on the activity images. In reconstruction, the attenuation map may be used to correct the attenuation effect in the corrected imaging data. For example, in Equations (3) and (4), the attenuation map is integrated into the projection matrix $H_{i,j}$.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, at least two of operations 1110-1130 may be performed simultaneously or in turn.

Figure 15A:
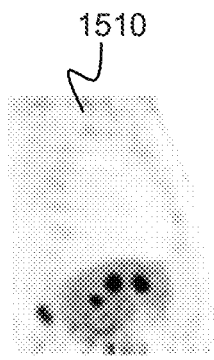
FIGS. 15A and 15B are schematic diagrams illustrating exemplary images generated based on different motion vector fields (MVFs) according to some embodiments of the present disclosure.
Figure 15B:
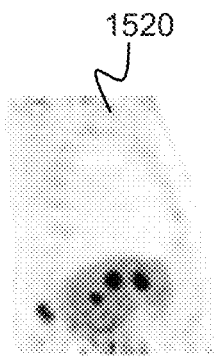
Figure 15C:
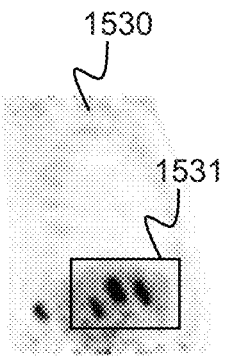
FIG. 15C is a schematic diagram illustrating an exemplary image generated without motion compensation.

FIG. 15A is a schematic diagram illustrating an exemplary image 1510 generated based on MVFs estimated using the first MVF estimation approach according to some embodiments of the present disclosure. FIG. 15B is a schematic diagram illustrating an exemplary image 1520 generated based on MVFs estimated using the third MVF estimation approach according to some embodiments of the present disclosure. FIG. 15C is a schematic diagram illustrating an exemplary image 1530 generated without motion compensation (or motion correction). As illustrated, images 1510 and 1520 have higher image quality than image 1530. For example, region 1531 in image 1530 includes motion blurring that is invisible in images 1510 and 1520 in FIGS. 15A and 15B, respectively.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 16A:
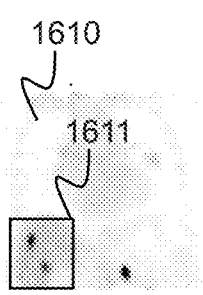
FIGS. 16A and 16B are schematic diagrams illustrating exemplary images generated without motion compensation.
Figure 16C:
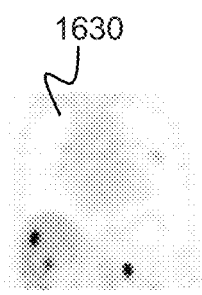
FIGS. 16C and 16D are schematic diagrams illustrating exemplary images generated using motion compensation according to some embodiments of the present disclosure.
Figure 16E:
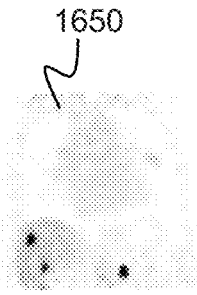
FIGS. 16E and 16F are schematic diagrams illustrating exemplary images generated using conventional motion compensation.
Figure 16B:
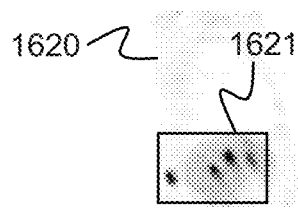
Figure 16D:
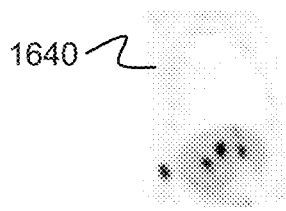
Figure 16F:
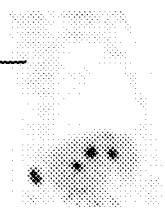

FIGS. 16A and 16B are schematic diagrams illustrating exemplary images 1610 and 1620 generated without motion compensation (or motion correction). FIGS. 16C and 16D are schematic diagrams illustrating exemplary images 1630 and 1640 generated using motion compensation (or motion correction) according to some embodiments of the present disclosure. FIGS. 16E and 16F are schematic diagrams illustrating exemplary images 1650 and 1660 generated using conventional motion compensation. As illustrated, images 1630 through 1660 have higher image quality than images 1610 and 1620. For example, region 1611 in image 1610 and region 1621 in image 1620 include motion blurring that is invisible in images 1630 through 1660 in FIGS. 16C through 16F, respectively.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. An imaging system, comprising:
    at least one storage device including a set of instructions; and
    at least one processor configured to communicate with the at least one storage device, wherein when executing the set of instructions, the at least one processor is configured to direct the system to perform operations including:
        obtaining original imaging data of an object in a raw-data domain, the original imaging data being acquired by an imaging device, the original imaging data including original time of flight (TOF) information and being subject to non-rigid motion of the object;
        gating the original imaging data into a plurality of data sets in the raw-data domain each of which corresponds to a motion phase of the non-rigid motion;
        determining a plurality of motion vector fields (MVFs) based on the plurality of data sets, the plurality of motion vector fields indicating the non-rigid motion, each of the plurality of motion vector fields corresponding to one of the plurality of data sets;
        for an original line of response (LOR) of one of at least one of the plurality of data sets, dividing, based on the original TOF information, the original LOR into a plurality of original LOR sections;
        generating corrected imaging data in the raw-data domain by performing, based on the corresponding MVF of the plurality of MVFs, rigid transformation on the plurality of original LOR sections of one of at least one of the plurality of data sets; and
    generating one or more target images of the object by performing, based on the corrected imaging data, image reconstruction.

2. The system of claim 1, wherein a length of each of the plurality of original LOR sections depends on temporal resolution of the original TOF information.

3. The system of claim 1, wherein generating the corrected imaging data by performing, based on the corresponding MVF, the rigid transformation on the plurality of original LOR sections includes:
    for each of the plurality of original LOR sections of the original LOR of the data set, determining a transformed LOR section by performing, based on the corresponding MVF, the rigid transformation on the original LOR section; and
    generating the corrected imaging data based on the transformed LOR sections.

4. The system of claim 3, wherein generating the corrected imaging data by performing, based on the corresponding MVF, rigid transformation on the plurality of original LOR sections further includes:
    for each of the transformed LOR sections, determining transformed TOF information corresponding to the transformed LOR section by performing, based on the corresponding MVF, the rigid transformation on the original TOF information of the corresponding original LOR section; and
    generating the corrected imaging data based further on the transformed TOF information corresponding to the transformed LOR sections.

5. The system of claim 3, wherein generating the corrected imaging data by performing, based on the corresponding MVF, rigid transformation on the plurality of original LOR sections further includes:
    for each of the transformed LOR sections, determining, based on the corresponding MVF and the rigid transformation on original detector locations of two first detector units, transformed detector locations of two second detector locations, the two first detector units being two of a plurality of detector units of the imaging device and corresponding to the original LOR, and the two second detector units being two of the plurality of detector units of the imaging device and corresponding to the transformed LOR section; and
    generating the corrected imaging data based further on the transformed detector locations corresponding to the each of the transformed LOR sections.

6. The system of claim 5, wherein the at least one processor is configured to direct the system to perform the operations including:
    generating a sensitivity map based on the transformed detector locations corresponding to the each of the transformed LOR sections; and
    generating the one or more target images of the object based further on the sensitivity map.

7. The system of claim 3, wherein the original LOR that is a straight line is transformed, due to the non-rigid motion, into an effective LOR that is a non-straight line.

8. The system of claim 7, wherein the effective LOR is approximated by the transformed LOR sections corresponding to the plurality of original LOR sections of the original LOR.

9. The system of claim 3, wherein each of the transformed LOR sections is a straight line.

10. The system of claim 1, wherein the one of the at least one of the plurality of data set includes a plurality of coincidence events corresponding to the original LOR, each of the plurality of original LOR sections corresponding to one of the plurality of coincidence events.

11. The system of claim 1, wherein the original imaging data in the raw-data domain includes listmode data or sinogram data.

12. The system of claim 1, wherein the non-rigid motion includes respiration motion or cardiac motion of the object.

13. The system of claim 1, wherein generating the one or more images of the object based on the corrected imaging data includes:
obtaining an attenuation map of the object; and
generating the one or more target images of the object based on the corrected imaging data and the attenuation map.

14. The system of claim 13, wherein obtaining an attenuation map of the object includes:
determining the attenuation map based on the plurality of motion vector fields.

15. An imaging method implemented on a machine including one or more processors and one or more storage devices, comprising:
obtaining original imaging data of an object in a raw-data domain, the original imaging data being acquired by an imaging device, the original imaging data including original time of flight (TOF) information and being subject to non-rigid motion of the object;
gating the original imaging data into a plurality of data sets in the raw-data domain each of which corresponds to a motion phase of the non-rigid motion;
determining a plurality of motion vector fields (MVFs) based on the plurality of data sets, the plurality of motion vector fields indicating the non-rigid motion, each of the plurality of motion vector fields corresponding to one of the plurality of data sets;
for an original line of response (LOR) of one of at least one of the plurality of data sets, dividing, based on the original TOF information, the original LOR into a plurality of original LOR sections;
generating corrected imaging data in the raw-data domain by performing, based on the corresponding MVF of the plurality of MVFs, rigid transformation on the plurality of original LOR sections of one of at least one of the plurality of data sets; and
generating one or more target images of the object by performing, based on the corrected imaging data, image reconstruction.

16. The method of claim 15, wherein a length of each of the plurality of original LOR sections depends on temporal resolution of the original TOF information.

17. The method of claim 15, wherein generating the corrected imaging data by performing, based on the corresponding MVF, the rigid transformation on the plurality of original LOR sections includes:
for each of the plurality of original LOR sections of the original LOR of the data set, determining a transformed LOR section by performing, based on the corresponding MVF, the rigid transformation on the original LOR section; and
generating the corrected imaging data based on the transformed LOR sections.

18. A non-transitory computer readable medium, comprising at least one set of instructions for imaging, wherein when executed by one or more processors of a computing device, the at least one set of instructions causes the computing device to perform a method, the method comprising:
obtaining original imaging data of an object in a raw-data domain, the original imaging data being acquired by an imaging device, the original imaging data including original time of flight (TOF) information and being subject to non-rigid motion of the object;
gating the original imaging data into a plurality of data sets in the raw-data domain each of which corresponds to a motion phase of the non-rigid motion;
determining a plurality of motion vector fields(MVFs) based on the plurality of data sets, the plurality of motion vector fields indicating the non-rigid motion, each of the plurality of motion vector fields corresponding to one of the plurality of data sets;
for an original line of response (LOR) of one of at least one of the plurality of data sets, dividing, based on the original TOF information, the original LOR into a plurality of original LOR sections;
generating corrected imaging data in the raw-data domain by performing, based on the corresponding MVF of the plurality of MVFs, rigid transformation on the plurality of original LOR sections of one of at least one of the plurality of data sets; and
generating one or more target images of the object by performing, based on the corrected imaging data, image reconstruction.

19. The non-transitory computer readable medium of claim 18, wherein the original LOR that is a straight line is transformed, due to the non-rigid motion, into an effective LOR that is a non-straight line.

20. The non-transitory computer readable medium of claim 19, wherein the effective LOR is approximated by the transformed LOR sections corresponding to the plurality of original LOR sections of the original LOR.

* * * * *